(12) United States Patent
Burditt

(10) Patent No.: US 11,147,589 B2
(45) Date of Patent: Oct. 19, 2021

(54) MOTORIZED CALLUS REMOVER APPARATUS

(71) Applicant: Connie Burditt, Prior Lake, MN (US)

(72) Inventor: Connie Burditt, Prior Lake, MN (US)

( * ) Notice: Subject to any disclaimer, the term of this patent is extended or adjusted under 35 U.S.C. 154(b) by 352 days.

(21) Appl. No.: 16/419,056

(22) Filed: May 22, 2019

(65) Prior Publication Data

US 2020/0367934 A1    Nov. 26, 2020

(51) Int. Cl.
*A61B 17/54* (2006.01)
*A61B 17/00* (2006.01)
*A61B 17/32* (2006.01)

(52) U.S. Cl.
CPC .... *A61B 17/54* (2013.01); *A61B 2017/00367* (2013.01); *A61B 2017/00761* (2013.01); *A61B 2017/320004* (2013.01)

(58) Field of Classification Search
CPC ............ A61B 17/54; A61B 17/545; A61B 2017/00367; A61B 2017/00761; A61B 2017/320004; A61B 2017/320008
See application file for complete search history.

(56) References Cited

U.S. PATENT DOCUMENTS

| | | | |
|---|---|---|---|
| 6,178,970 B1* | 1/2001 | Purifoy | A61B 17/54 132/73.5 |
| 7,581,545 B1* | 9/2009 | Moldawski | A45D 40/22 132/73.6 |
| 8,343,116 B2 | 1/2013 | Ignon | |
| 9,788,860 B2* | 10/2017 | Smith | A61B 17/54 |
| 2002/0050278 A1 | 5/2002 | Jo | |
| 2007/0123808 A1* | 5/2007 | Rhoades | A46B 5/0016 601/73 |
| 2009/0004953 A1 | 1/2009 | Kinsey | |
| 2009/0301507 A1 | 12/2009 | Tes | |
| 2011/0226269 A1 | 9/2011 | Routhier | |

\* cited by examiner

*Primary Examiner* — Jocelin C Tanner

(57) ABSTRACT

A motorized callus remover apparatus for easily removing calluses includes a hollow having a motor cavity. A motor is coupled within the motor cavity and oscillates. A plurality of controls is coupled to the handle to operate a motor coupled within the motor cavity. A neck is coupled to the motor and extends through the distal end of the handle. The motor oscillates the neck. A hollow head has a sleeve aperture extending through a back side to a collection cavity to selectively receive the neck. The head oscillates with the neck when with motor is engaged. A sandpaper sheet is selectively engageable with the bottom side of the head and has a plurality of second catch apertures corresponding with a plurality of first catch apertures of the bottom side to collect skin particles.

11 Claims, 3 Drawing Sheets

MOTORIZED CALLUS REMOVER APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to callus removers and more particularly pertains to a new callus remover for easily removing calluses.

BRIEF SUMMARY OF THE INVENTION

An embodiment of the disclosure meets the needs presented above by generally comprising a handle having a proximal end, a distal end, and a sidewall extending therebetween. The handle is hollow and has a motor cavity. A motor is coupled within the motor cavity and oscillates. A plurality of controls is coupled to the handle and is in operational communication with the motor. A power source is coupled within the motor cavity and is in operational communication with the motor and the plurality of controls. The power source has a power cord extending through the proximal end of the handle. A neck is coupled to the motor and extends through the distal end of the handle. The motor oscillates the neck. A hollow head has a sleeve aperture extending through a back side to a collection cavity to selectively receive the neck. A bottom side of the head has a plurality of first catch apertures extending through to the collection cavity. The head oscillates with the neck when with motor is engaged. A sandpaper sheet is selectively engageable with the bottom side of the head and has a plurality of second catch apertures corresponding with the plurality of first catch apertures of the bottom side. The plurality of second catch apertures and the plurality of first catch apertures are configured to collect skin particles.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
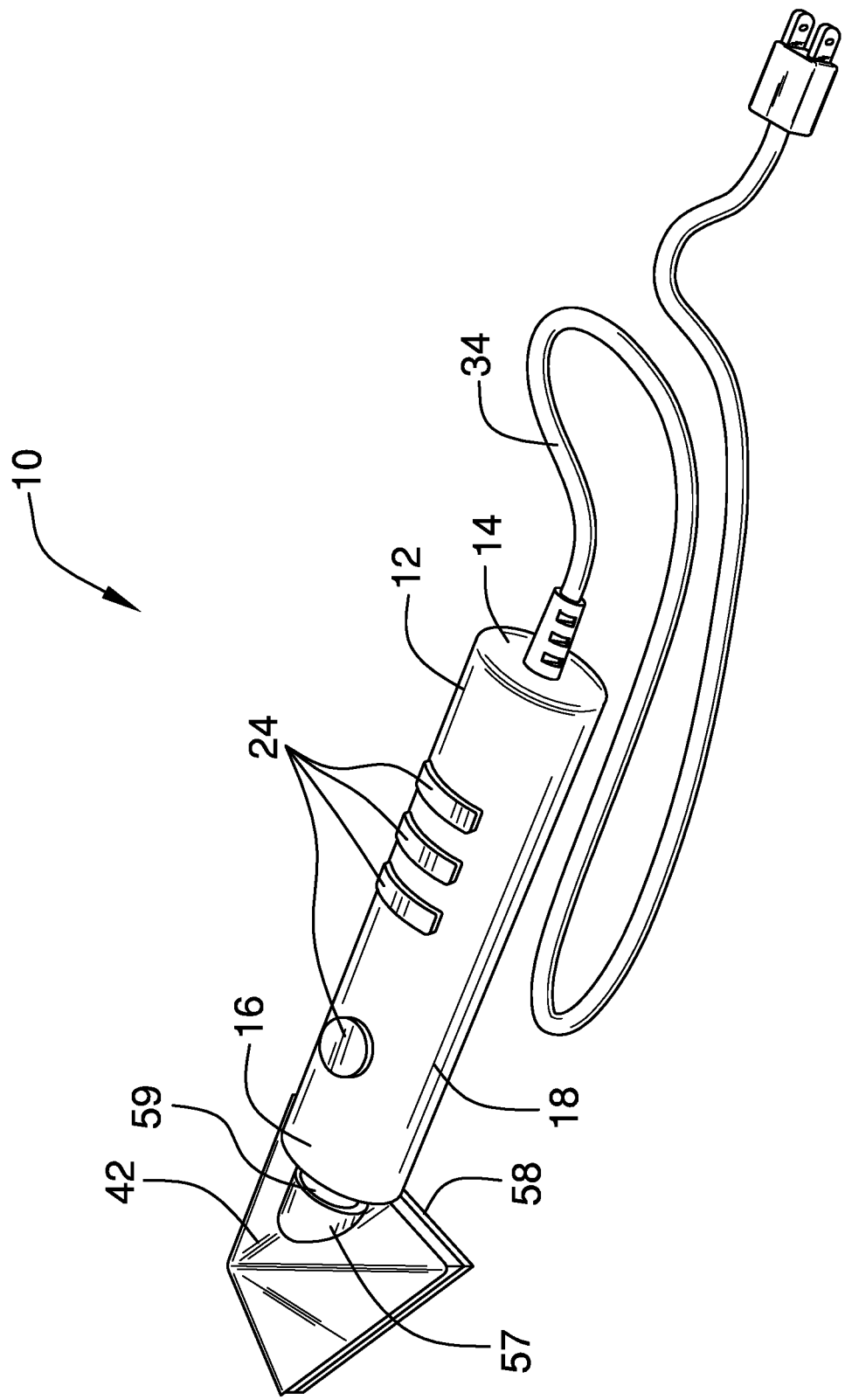
FIG. 1 is an isometric view of a motorized callus remover apparatus according to an embodiment of the disclosure.
Figure 2:
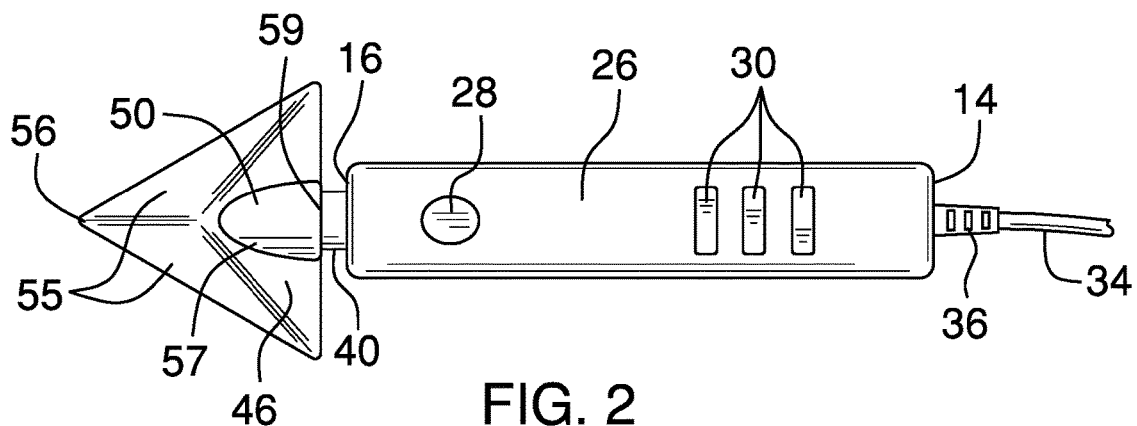
FIG. 2 is a top plan view of an embodiment of the disclosure.
Figure 3:
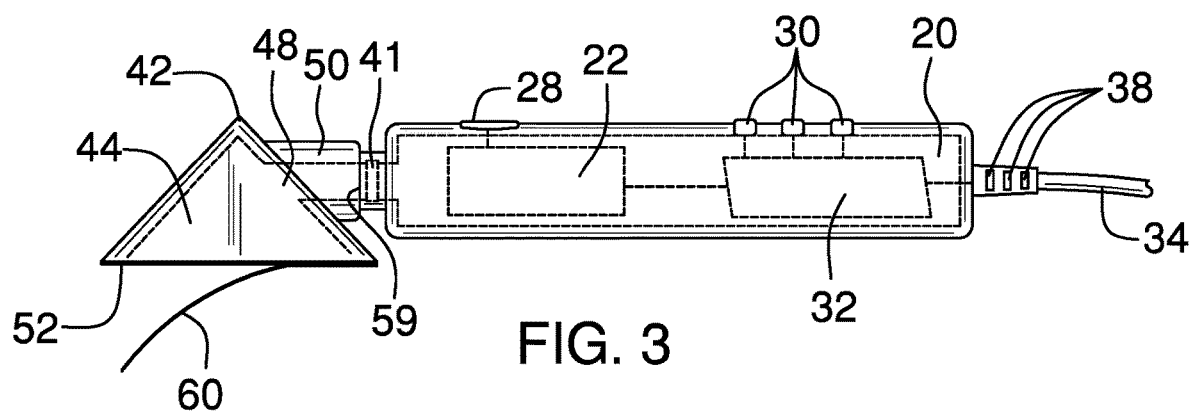
FIG. 3 is a side elevation view of an embodiment of the disclosure.
Figure 4:
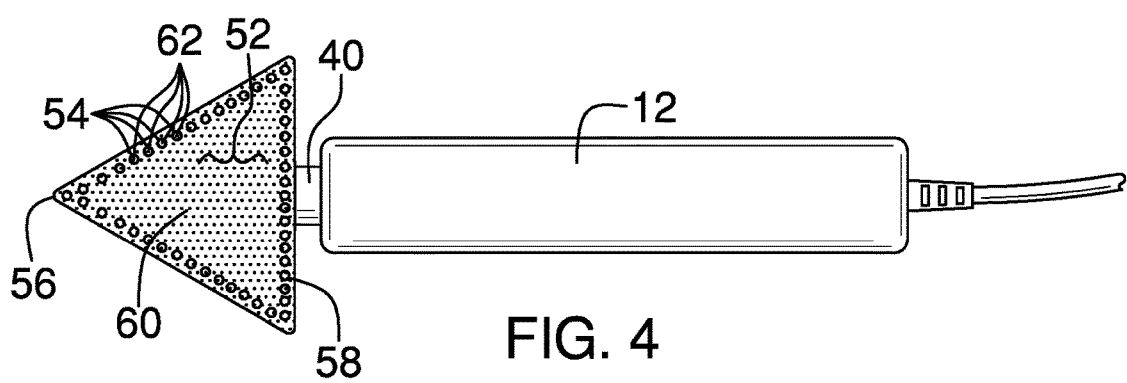
FIG. 4 is a bottom plan view of an embodiment of the disclosure.
Figure 5:
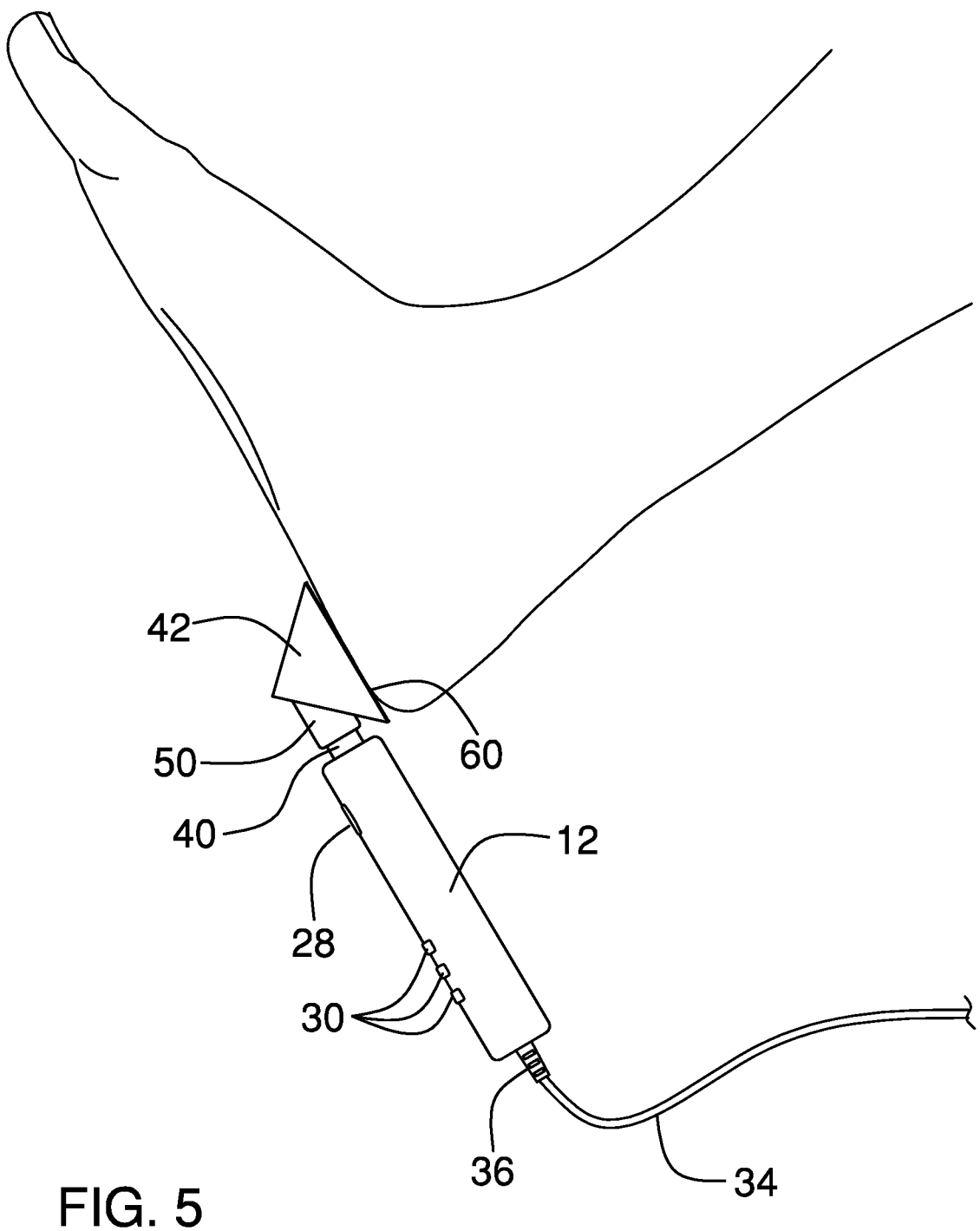
FIG. 5 is an in-use view of an embodiment of the disclosure.

With reference now to the drawings, and in particular to FIGS. 1 through 5 thereof, a new callus remover embodying the principles and concepts of an embodiment of the disclosure and generally designated by the reference numeral 10 will be described.

As best illustrated in FIGS. 1 through 5, the motorized callus remover apparatus 10 generally comprises a cylindrical handle 12 having a proximal end 14, a distal end 16, and a sidewall 18 extending therebetween. The handle 12 is hollow and has a motor cavity 20 with a motor 22 coupled therein. The motor 22 is an oscillator and may also have a vacuum. A plurality of controls 24 is coupled within a dorsal side 26 of the sidewall 18. The plurality of controls 24 may comprise a circular power button 28 and a plurality of rectangular speed control buttons 30. The plurality of controls 24 is in operational communication with the motor 22 to turn the motor 22 on and off as well as to manipulate the speed of the oscillation for user comfort. A power source 32 is coupled within the motor cavity 20 and is in operational communication with the motor 22 and the plurality of controls 24. The power source 32 has a power cord 34 extending through the proximal end 14 of the handle and has a cord reinforcement 36 coupled around the power cord 34 adjacent the proximal end 14 of the handle. The cord reinforcement 36 is tapered and has a plurality of flex channels 38 to provide a limited range of movement to protect the power cord 34.

A tubular neck 40 is coupled to the motor 22 extends through the distal end 16 of the handle. The motor 22 oscillates the neck 40 and is also in fluid communication with the neck 40 to draw air. A filter 41 may be installed within the neck 40. A head 42 is coupled to the neck 40. The head 42 is hollow and has a collection cavity 44. A back side 46 of the head has a sleeve aperture 48 extending through to the collection cavity 44 and a tubular sleeve extension 50 extending around the sleeve aperture 48 to selectively receive the neck 40. The head 42 may be a triangular prism with a triangular bottom side 52 having a plurality of first catch apertures 54 extending through to the collection cavity 44. The bottom side 52, the back side 46, and each of a pair of lead sides 55 may be equilateral triangles. The triangular bottom side 52 allows a user to have precision with a lead tip 56 but also cover a larger surface area when desired by applying the whole bottom side 52 to the foot. The plurality of first catch apertures 54 is aligned along the perimeter of the bottom side 52 with minimal spacing between each catch aperture 54. The motor 22 draws air through the plurality of first catch apertures 54 when the head 42 is attached to the neck 40. The sleeve extension 50 has a central axis lying in a plane parallel to a plane of the bottom side 52 and the sleeve extension 50, the neck 40, and the handle 12 are all coaxial when engaged. The sleeve extension 50 thus has an angled edge 57 contacting the back side 46 and a straight edge 59 lying in a plane perpendicular to the plane of the bottom side. The sleeve extension 50 does not extend past a back edge 58 of the bottom side 52 to prevent interference between the handle 12 and the head 42. The inner diameter of the sleeve extension 50 matches the outer diameter of the neck 40 for selective engagement, and the outer diameter of the sleeve extension 50 is less than the diameter of the handle 12. A sandpaper sheet 60 is selectively engageable with the bottom side 52 of the head and has a plurality of second catch apertures 62 corresponding with the plurality of first catch apertures 54 of the bottom side.

In use, the plurality of controls 24 is used to operate the motor 22 to cause the head 42 to oscillate with the neck 40. The sandpaper sheet 60 removes calluses on the user's feet and the plurality of second catch apertures 62 and the plurality of first catch apertures 54 are configured to collect skin particles in to the collection cavity 44, particularly with the vacuum element drawing air. The plurality of speed control buttons 30 may be used to increase and alternatively decrease the intensity of the oscillation to adjust efficacy and comfort. When finished, the motor 22 is turned off and the head 42 may be removed and the collected skin particles emptied through the sleeve aperture 48.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A motorized callus remover apparatus comprising:
    a handle, the handle having a proximal end, a distal end, and a sidewall extending therebetween, the handle being hollow and having a motor cavity;
    a motor coupled to the handle, the motor configured to oscillate and being coupled within the motor cavity;
    a plurality of controls coupled to the handle, the plurality of controls being in operational communication with the motor;
    a power source coupled to the handle, the power source being coupled within the motor cavity and in operational communication with the motor and the plurality of controls, the power source having a power cord extending through the proximal end of the handle;
    a neck coupled to the motor, the neck extending through the distal end of the handle, the motor configured to oscillate the neck;
    a head coupled to the neck, the head being hollow and having a collection cavity, a back side having a sleeve aperture extending through to the collection cavity to selectively receive the neck, and a bottom side having a plurality of first catch apertures extending through to the collection cavity, the head configured to oscillate with the neck when motor is engaged; and
    a sandpaper sheet coupled to the head, the sandpaper sheet being selectively engageable with the bottom side of the head and having a plurality of second catch apertures corresponding with the plurality of first catch apertures of the bottom side, the plurality of second catch apertures and the plurality of first catch apertures being configured to collect skin particles.

2. The motorized callus remover apparatus of claim 1 further comprising the head being a triangular prism, the bottom side being triangular and the back side having a sleeve extension surrounding the sleeve aperture to selectively receive the neck, each of the sleeve extension and the neck being tubular.

3. The motorized callus remover apparatus of claim 2 further comprising the sleeve extension having a central axis lying in a plane parallel to a plane of the bottom side, the sleeve extension, the neck, and the handle being coaxial when engaged.

4. The motorized callus remover apparatus of claim 2 further comprising the bottom side being an equilateral triangle.

5. The motorized callus remover apparatus of claim 1 further comprising the handle being cylindrical.

6. The motorized callus remover apparatus of claim 5 further comprising each of the plurality of controls being coupled within a dorsal side of the sidewall, the plurality of controls comprising a power button and a plurality of speed control buttons.

7. The motorized callus remover apparatus of claim 6 further comprising each of the plurality of speed control buttons being rectangular and the power button being circular.

8. The motorized callus remover apparatus of claim 1 further comprising the plurality of first catch apertures being aligned along the perimeter of the bottom side.

9. The motorized callus remover apparatus of claim 1 further comprising the power source having a cord reinforcement coupled around the power cord adjacent the proximal end of the handle, the cord reinforcement being tapered and having a plurality of flex channels to provide a limited range of movement to protect the power cord.

10. The motorized callus remover apparatus of claim 1 further comprising the motor having a vacuum and being in fluid communication with the neck, the motor drawing air through the plurality of first catch apertures when the head is attached to the neck.

11. A motorized callus remover apparatus comprising:
a cylindrical handle, the handle having a proximal end, a distal end, and a sidewall extending therebetween, the handle being hollow and having a motor cavity;
a motor coupled to the handle, the motor being coupled within the motor cavity, the motor configured to oscillate and having a vacuum;
a plurality of controls coupled to the handle, each of the plurality of controls being coupled within a dorsal side of the sidewall, the plurality of controls comprising a circular power button and a plurality of rectangular speed control buttons, the plurality of controls being in operational communication with the motor;
a power source coupled to the handle, the power source being coupled within the motor cavity and in operational communication with the motor and the plurality of controls, the power source having a power cord extending through the proximal end of the handle, the power source having a cord reinforcement coupled around the power cord adjacent the proximal end of the handle, the cord reinforcement being tapered and having a plurality of flex channels to provide a limited range of movement to protect the power cord;
a neck coupled to the motor, the neck being tubular and extending through the distal end of the handle, the motor configured to oscillate, and being in fluid communication with, the neck;
a head coupled to the neck, the head being a triangular prism, the head being hollow and having a collection cavity, a back side having a sleeve aperture extending through to the collection cavity and a tubular sleeve extension extending around the sleeve aperture to selectively receive the neck, and a triangular bottom side having a plurality of first catch apertures extending through to the collection cavity, the plurality of first catch apertures being aligned along the perimeter of the bottom side, the motor configured to draw air through the plurality of first catch apertures when the head is attached to the neck; the sleeve extension having a central axis lying in a plane parallel to a plane of the bottom side, the sleeve extension, the neck, and the handle being coaxial when engaged, the head configured to oscillate with the neck when motor is engaged; and
a sandpaper sheet coupled to the head, the sandpaper sheet being selectively engageable with the bottom side of the head and having a plurality of second catch apertures corresponding with the plurality of first catch apertures of the bottom side, the plurality of second catch apertures and the plurality of first catch apertures being configured to collect skin particles.

\* \* \* \* \*